United States Patent [19]

Satoru et al.

[11] Patent Number: 4,686,372

[45] Date of Patent: Aug. 11, 1987

[54] METHOD AND APPARATUS FOR MEASURING CELL COUNTS OF METHANOGENS OR METHANE PRODUCING ACTIVITY THEREOF

[75] Inventors: Isoda Satoru, Takarazuka; Inatomi Kenichi, Itami, both of Japan

[73] Assignee: Mitsubishi Denki Kabushiki Kaisha, Tokyo, Japan

[21] Appl. No.: 694,384

[22] PCT Filed: May 7, 1984

[86] PCT No.: PCT/JP84/00230

§ 371 Date: Jan. 9, 1985

§ 102(e) Date: Jan. 9, 1985

[87] PCT Pub. No.: WO84/04544

PCT Pub. Date: Nov. 22, 1984

[30] Foreign Application Priority Data

May 9, 1983 [JP] Japan .................................. 58-81912
Feb. 28, 1984 [JP] Japan .................................. 59-38311

[51] Int. Cl.⁴ .............................................. G01N 21/64
[52] U.S. Cl. .................................. 250/461.2; 250/301
[58] Field of Search ............ 250/301, 302, 364, 461.1, 250/461.2; 73/53; 435/39

[56] References Cited

U.S. PATENT DOCUMENTS 3,566,114 2/1971 Brewer ............................. 250/461.2
4,112,741 7/1978 Kerfoot et al. ................... 250/461.1
4,503,149 3/1985 Boyd ............................... 250/461.2

OTHER PUBLICATIONS

Biochemistry, 17, pp. 4583-4593 ('78).
J. of Bacteriology, 121, pp. 184-191 ('75).
J. of Bacteriology, 112, pp. 527-531 ('72).
R. Braun: Methangarung Organischer Abfallstoffe, Springer-verlag, Wien-New York, 1982, Seiten 145-149.
Howard A Strobel: Chemical Instrumentation, A Systematic Approach, 2nd editon, Addison-Wesley Publishing Co., 1973, pp. 422-426.

Primary Examiner—Janice A. Howell
Attorney, Agent, or Firm—Oblon, Fisher, Spivak, McClelland & Maier

[57] ABSTRACT

A method for measuring cell counts or methane producing activity of Methanogens in an object for examination containing therein Methanogens, in which excited light of a particular wavelength region is irradiated onto the object for examination, and intensity of fluorescence of a particular wavelength region, which the object for examination radiates, is measured. Since, according to this invention, intensity of fluorescence specific to Methanogens is measured, it is possible to measure with high precision the cell counts or the methane producing activity of Methanogens existing in a multitude of microorganism groups and foreign substances such as digested sludge, etc. in a methane fermentation tank, etc. of a sewage treatment system, in particular.

12 Claims, 12 Drawing Figures

METHOD AND APPARATUS FOR MEASURING CELL COUNTS OF METHANOGENS OR METHANE PRODUCING ACTIVITY THEREOF

FIELD OF TECHNOLOGY

This invention relates to a method and apparatus for measuring cell counts of Methanogens or methane producing activity thereof in an object for examination having Methanogens therein. More particularly, it is concerned with a method which is applicable to measurement of the cell counts of Methanogens or the methane producing activity of such microorganism existing in a multitude of microorganism groups and in foreign substances such as digested sludge, and so forth which are held in a methane fermentation tank of a sewage treatment system, or the like.

BACKGROUND OF TECHNOLOGY

FIG. 1 shows a conventional apparatus for conducting this type of measurment. In the drawing, a reference numeral 1 designates an object for examination; a numeral 2 refers to a light source; 3 denotes a power source for applying an electric potential to the light source 2; 4 represents a photoelectric multiplying tube; 5 a power source for applying an electric potential to the photoelectric multiplying tube 4; and 6 indicates a detector for measuring photo-current of the photoelectric multiplying tube 4.

Light emitted from the light source 2 passes through the object for examination 1 containing therein microorganism. The transmitted light is received by the photoelectric multiplying tube 4, and its intensity is measured by the detector 6 as a photocurrent value of the photoelectric multiplying tube 4. Since there is established a definite relationship between absorbance and concentration of microorganism existing in the above-mentioned object for examination 1, thus obtained, when a visible light is used as the light source, the concentration of microorganism can be evaluated by measuring the absorbance of the object for examination. As the result of, or, in connection with, this, the cell counts can be evaluated.

Also, as an other method for measuring the microorganism activity, there has been known a method for optical measurement of a quantity of biological substance relative to the energy metabolism which is called "ATP" (Adenosine Triphosphate) or "NAD(P)H" (Nicotinamide Adenine Dinucleotide(phosphate)) contained in microorganism.

As mentioned in the preceding, the conventional method for measuring the cell counts or the activity of microorganism is to measure the absorbance of an object for examination 1, on account of which such method is effective only if the object for examination 1 is composed of one kind of microorganism and contains no foreign substance such as sludge, etc. However, if the object for examination 1 is composed of many kinds of microorganisms and, moreover, if foreign substances are contained within the examined object, it was impossible to selectively measure the cell counts or activity of a particular kind of microorganism. Further, since ATP and NAD(P)H are biological substances existing in all kinds of microorganisms, the method is not suitable for measuring the cell counts or methane producing activity of Methanogens alone.

SUMMARY OF THE INVENTION

The present invention is an apparatus and method for measuring the cell counts or the methane producing activity of the above-mentioned Methanogens, by irradiating excited light of a particular wavelength range onto an object for examination containing therein Methanogens, and measuring the intensity of fluorescence of a particular wavelength region which the above-mentioned object for examination radiates. More particularly, the invention aims at providing a method and apparatus capable of measuring the cell counts or the methane producing activity of the above-mentioned Methanogens even if there is a mixed system of microorganism containing therein foreign substances such as digested sludge, etc. as in a methane fermentation tank.

According to the present invention, it is possible to determine with high precision the cell counts or the methane producing activity of Methanogens by use of light in a wavelength range of from 220 nm to 310 nm, or from 220 nm to 255 nm, or from 260 nm to 305 nm, or from 380 nm to 440 nm, as the excited light of a particular wavelength range to be irradiated onto the object for examination which contains therein Methanogens.

According to the present invention, it is possible to accurately measure the cell counts or the methane producing activity of Methanogens by measuring the intensity of the fluorescence in a wavelength range of from 330 nm to 370 nm, or from 450 nm to 490 nm, which the examining object radiates.

According to the present invention, it is possible to increase the measuring sensitivity by rendering the object for examination to be alkaline, or substituting solution which does not emit fluorescence of a range of the measuring wavelength in the excited wavelength range for the liquid component of the examining object, or diluting the object for examination.

PREFERRED EMBODIMENT OF THE INVENTION

Figure 1:
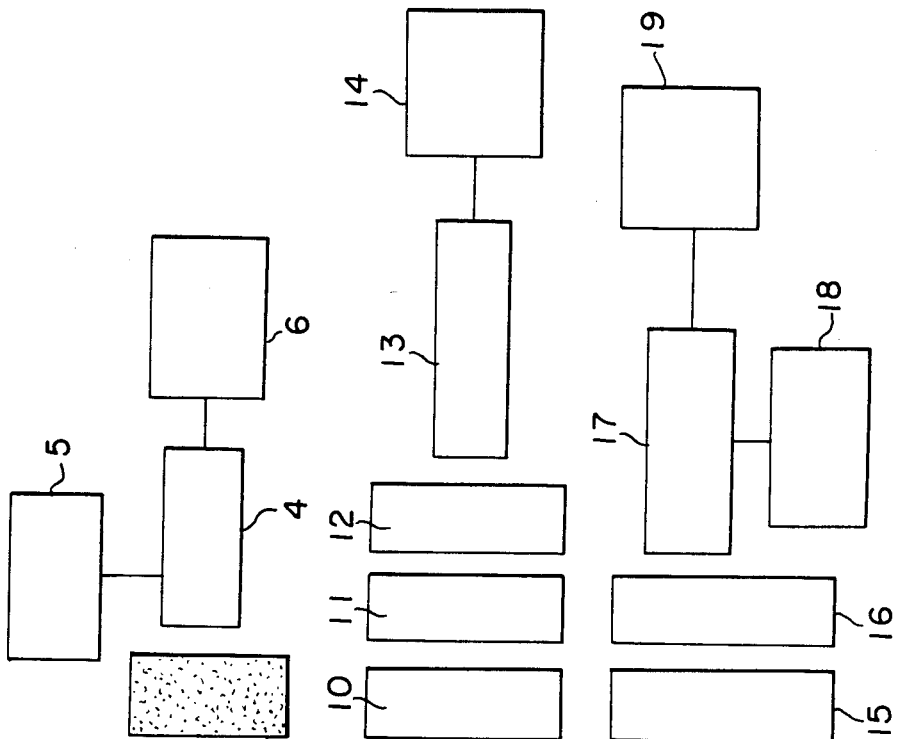
FIG. 1 is a block diagram for explanation of the conventional method for measuring cell counts of microorganism.
Figure 2:
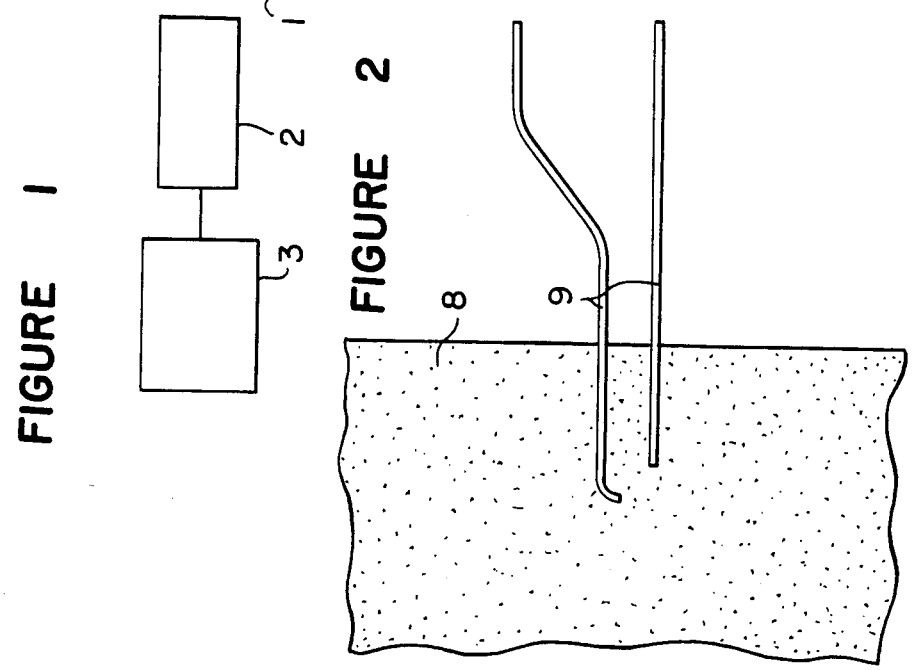
FIG. 2 is a block diagram for explanation of a method for measuring the cell counts or the methane producing activity of Methanogens according to one embodiment of the present invention.

In the following, the present invention will be described with reference to one embodiment as shown in the drawing. Referring now to FIG. 2, a reference numeral 8 designates the interior of a methane fermentation tank containing an object for examination; a numeral 9 refers to optical fibers to introduce and take out light into and from the fermentation tank 8; a numeral 10 denotes a light collecting device for collecting light emitted from a light source 13 into one of the optical fibers 9; a numeral 11 represents a selector to adjust intensity of light in the light source 13; a numeral 12 referes to an optical filter to limit a wavelength of light emitted from the light source 13; a numeral 14 indicates a power source for the light source; a numeral 15 represents a light collecting device for collecting light emitted from the other optical fiber 9; a numeral 16 refers to an optical filter to limit a wavelength of light at the light receiving side; a numeral 17 designates a photoelectric multiplying tube; a numeral 18 denotes a power source for the photoelectric multiplying tube; and a numeral 19 represents a detector for measuring photo-current in the photoelectric multiplying tube 17.

In the following, explanations will be given as to the principle and the function of the present invention. It has been known that Methanogens has physiological properties different from that of ordinary microorganisms and specific which are to it, although its electron transport system which takes part in the energy metabolism of Methanogens has not yet been clarified in its entirety. It is known that, in this electron transport system existing in the energy metabolism of the Methanogens, a substance called "Factor$_{420}$ ($F_{420}$)" functions as the electron carrier, which is a substance found in Methanogens and which is not existent in other biological bodies. Therefore, if the substance, which contain therein this substance $F_{420}$ as the principal component and takes part in the electron transport system of Methanogens possesses its physicochemical properties which are peculiar to it and and measurable, and are different from those of the microorganism groups other than Methanogens and foreign substances in the object for examination such as digested sludge, etc., and, moreover, if such properties are measurable in the state of viable cell (i.e., microorganism in its living state), such substance can be used as a parameter in measuring the cell counts or the methane producing activity of Methanogens. In particular, since the substance $F_{420}$, which takes part in the electron transport system of Methanogens as the principal component, it is directly related to the methane producing mechanism in its physiological function. Hence it can be an effective object, in the measurement of the methane producing activity.

As the result of strenuous efforts in studying and research done by the present inventor on the basis of this phenomenon, it has been clarified that the fluorscent property which is considered to be due to the substance $F_{420}$ in Methanogens takes different behaviour in the state of cell from the fluorescence properties to be ascribable to microorganisms other than Methanogens and to foreign substances in the digested sludge. Based on this clarification, the present invention has been completed.

Figure 3:
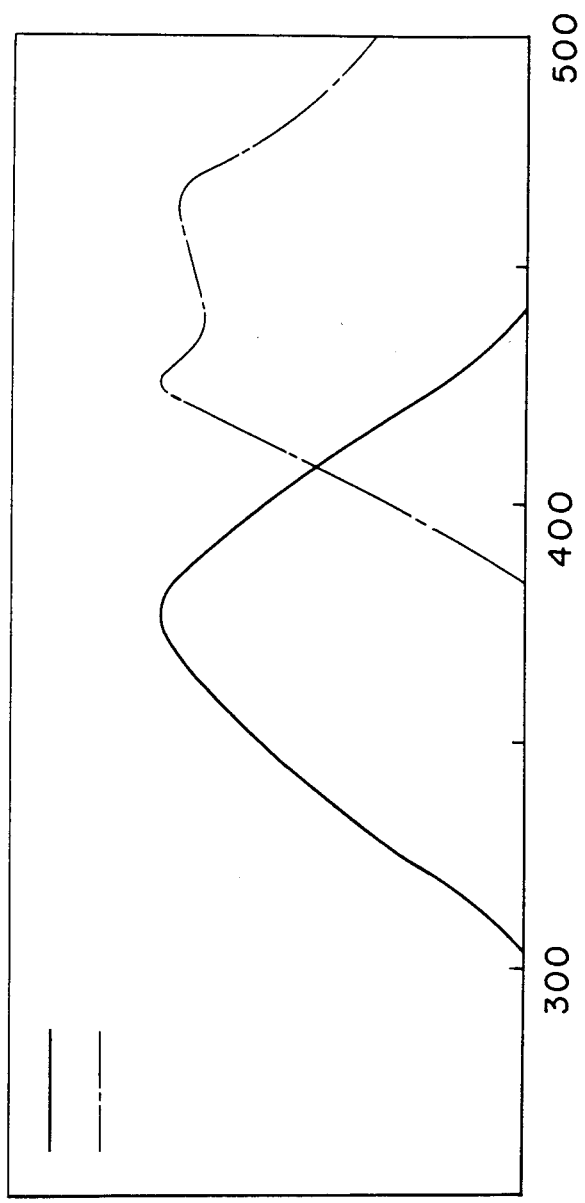
FIG. 3 is a graphical representation showing the fluorescence properties of a component model having components other than Methanogens in the digested sludge.

FIG. 3 indicates fluorescence excitation spectrum and fluorescence spectrum of *Escherichia coli* suspended in a nutrient medium (composed of 10 g/l of trypton, 10 g/l of sodium chloride, and 5 g/l of yeast extract). In the graphical representation, the fluorescence excitation spectrum indicates intensity of fluorescence in the wavelength of 470 nm with respect to changes in the excited wavelength, while the fluorescence spectrum indicates such fluorescence spectrum in the excited wavelength of 380 nm. The substances which radiate fluorescence in various biological substances, amino acids such as tryptophan, tyrosine, phenylalanine, and so forth are representative. However, those specimens used in this invention as the object for examination are all mixtures of these fluorescent substance, hence they may be regarded as a model of a biological specimen series other than Methanogens.

Figure 4:
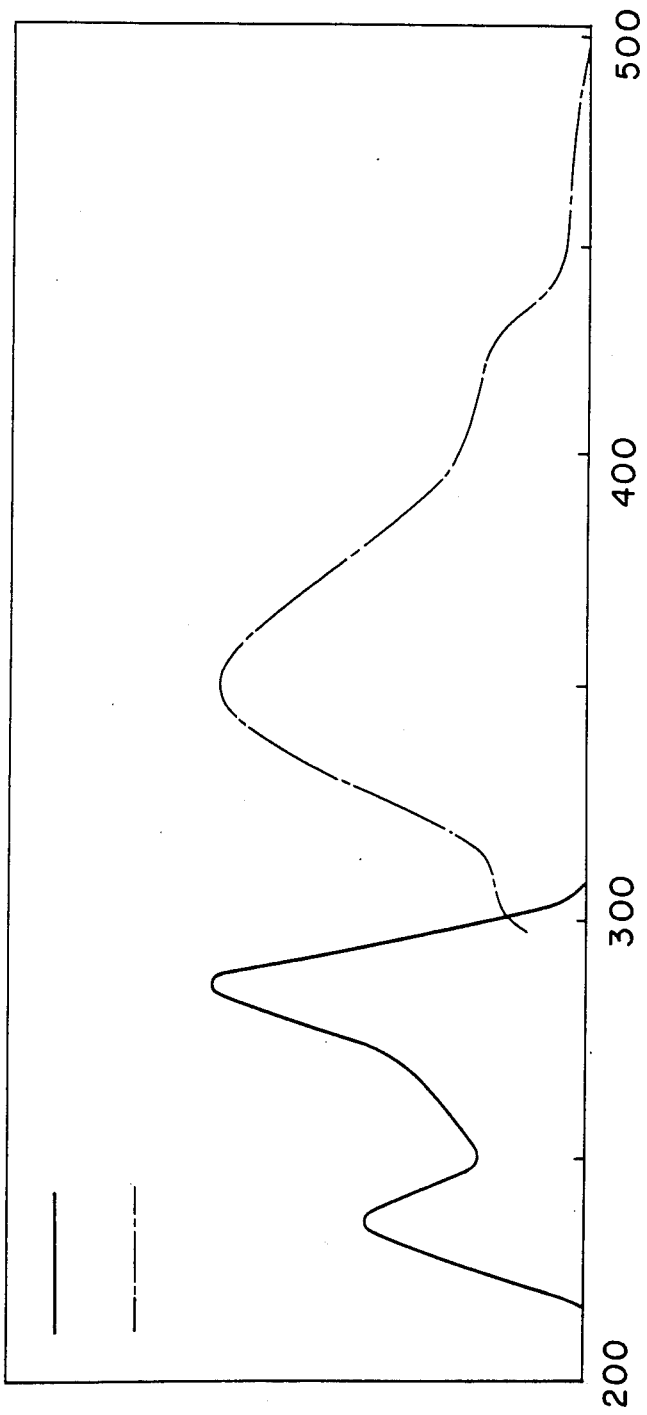
FIGS. 4 and 8 are graphical representations showing the fluorescence properties of Methanogens.

FIG. 4 shows fluorescence excitation spectrum and fluorescence spectrum of Methanogens (here, it is *Methanosarcina barkeri*) suspended in a minimum medium (a culture medium not containing therein any biological carbon source). In this case, since the minimum medium is used, no fluorescence from the culture medium can be observed. Therefore, the fluorescence properties shown in FIG. 4 is derived from Methanogens alone. As is apparent from comparison between FIGS. 3 and 4, the fluorescence properties of Methanogens takes different behaviour from the fluorescence properties of the specimen as used for the purpose of FIG. 3, i.e., the model specimen of the microorganism other than Methanogens and foreign substances.

Figure 5:
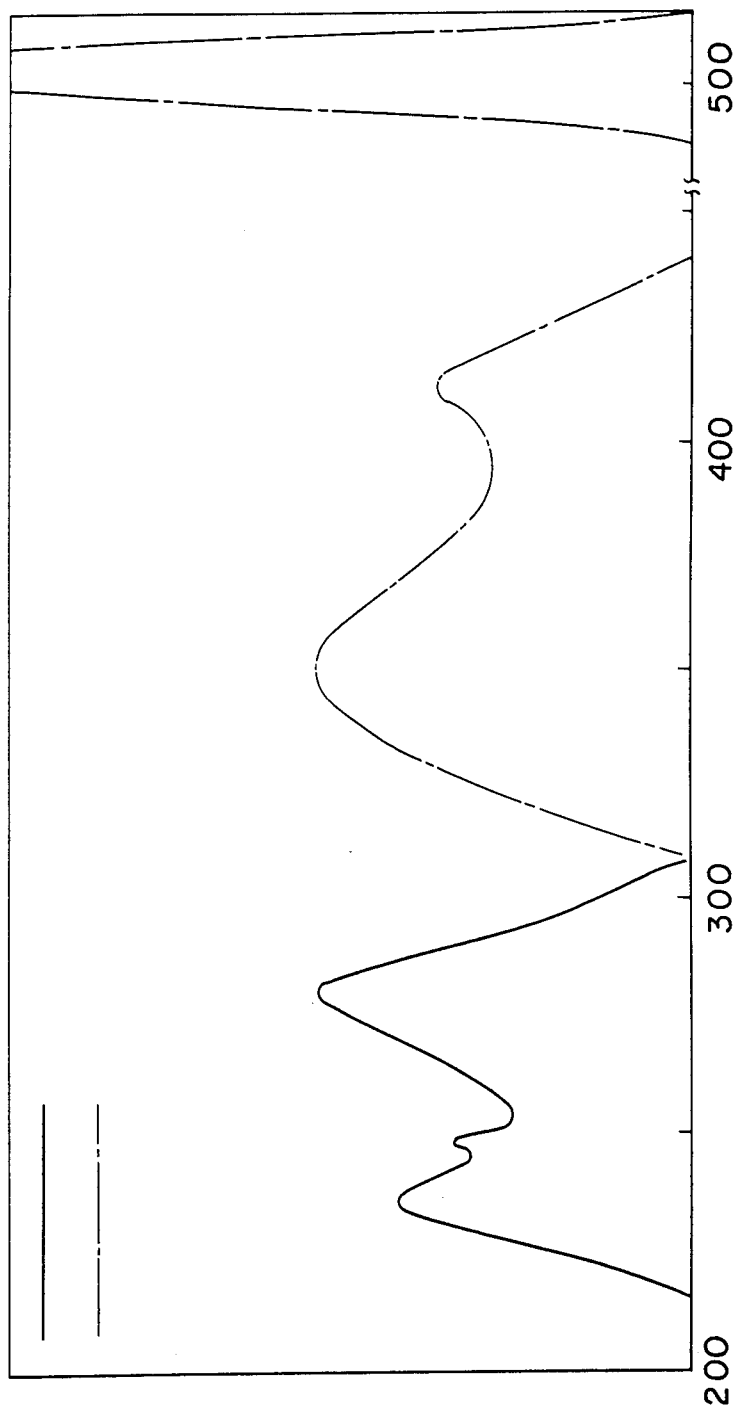
FIGS. 5 and 9 are graphical representations showing the fluorescence properties of digested sludge containing Methanogens.

FIG. 5 indicates fluorescence excitation spectrum and fluorescence spectrum of digested sludge sampled from a methane fermentation tank. Upon comparison of FIGS. 4 and 5, it will be seen that a well-matched behaviour is exhibited with the excitation light having a wavelength range of from 220 nm to 310 nm (in particular, having the respective peaks in the wavelength ranges of from 220 nm to 255 nm and from 260 nm to 305 nm) and the fluorescence having its wavelength range of from 330 nm to 370 nm, so that the fluorescence properties of the digested sludge in the above-mentioned wavelength range is ascribable to Methanogens. Also, it cannot be decided that, of the fluorescence properties shown in FIG. 5, the fluorescence spectrum of a wavelength range of from 380 nm to 450 nm is ascribable to Methanogens, because it is overlapping with the behaviour of the model of the biological specimen series other than Methanogens as shown in FIG. 3. Further, the fluorescence spectrum having its peak at the wavelength of 500 nm shown in FIG. 5 appears to be the fluorescence light from the component other than Methanogens in the digested sludge as the result of comparison between FIGS. 3 and 4.

Figure 8:
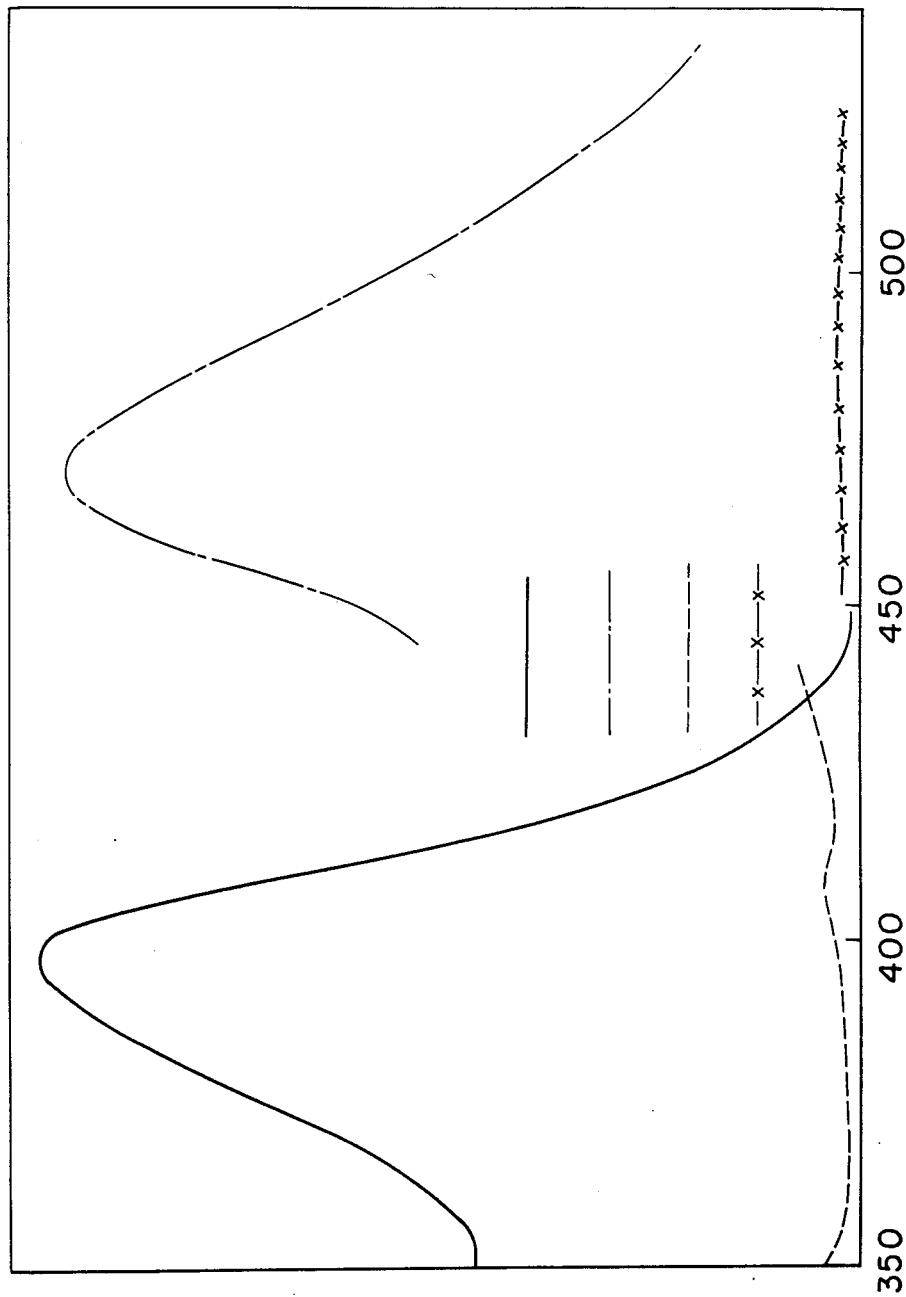

FIG. 8 indicates the fluorescence excitation spectrum and the fluorescence spectrum of Methanogens (here, it is *Methanosarcina barkeri*) suspended in a minimum culture medium (a culture medium not containing therein organic carbon source). For the sake of comparison, fluorescence excitation spectrum and the fluorescence spectrum of *Escherichia coli* suspended in the minimum medium are also shown. It should be noted here that the fluorescence excitation spectrum of Methanogens indicates an intensity of fluorescence having a wavelength of 470 nm with respect to changes in the excited wavelength, while the fluorescence spectrum indicates such fluorescence spectrum at the excited wavelength of 400 nm. Further, the fluorescence excitation spectrum of *Escherichia coli* indicates an intensity of fluorescence having a wavelength of 470 nm with respect to changes in the excited wavelength, while the fluorescence spectrum indicates such fluorescence spectrum at the excited wavelength of 400 nm. In this case, since the minimum medium is used, the fluorescence properties shown in FIG. 8 is derived from the microorganism alone, hence it is seen that the fluorescence properties of Methanogens takes a behaviour which is remarkably different from the fluorescence properties of *Escherichia coli*. Furthermore, from comparison with FIG. 3, it can be understood that the fluorescence properties of Methanogens takes a different behaviour from the fluorescence properties of the model specimen of microorganism other than Methanogens and foreign substances.

Figure 9:
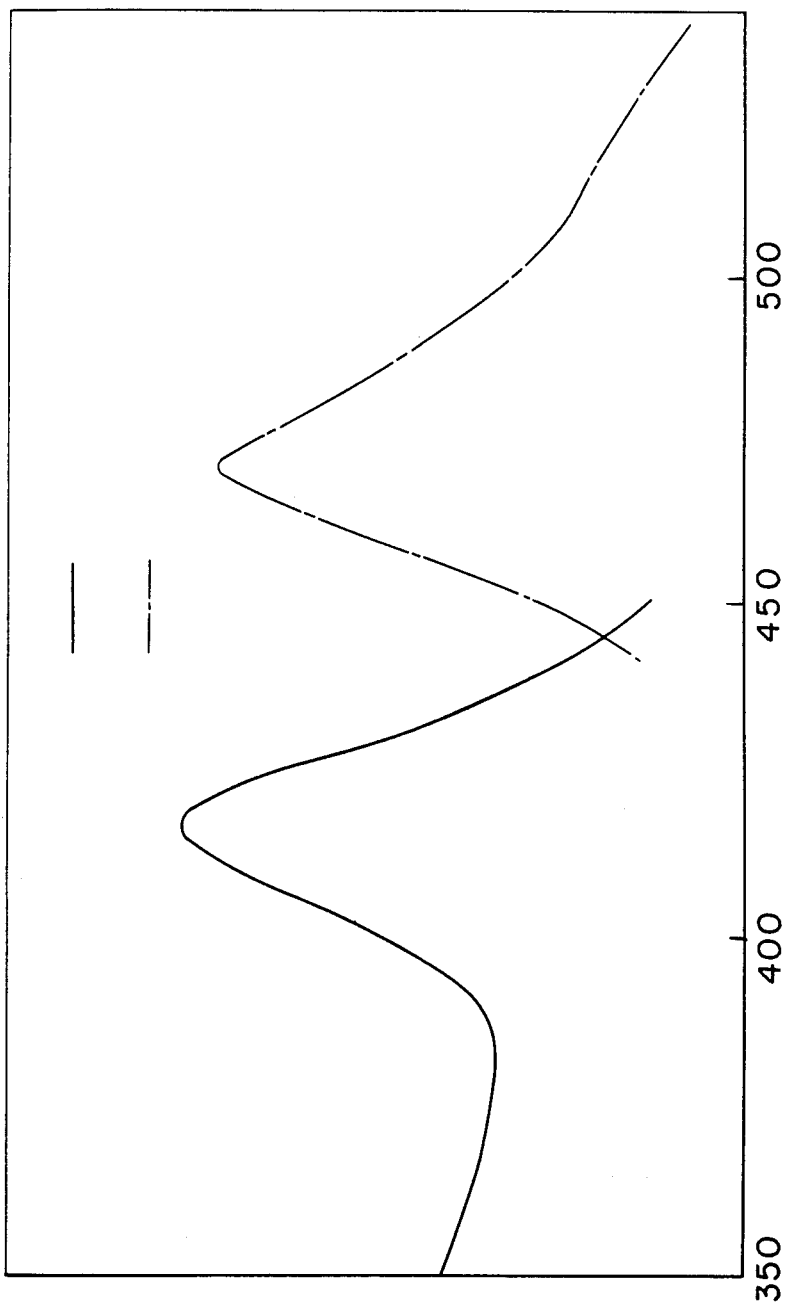

FIG. 9 shows the fluorescence excitation spectrum and the fluorescence spectrum of digested sludge sampled from a methane fermentation tank. In this case, the fluorescence excitation spectrum indicates an intensity of fluorescence having a wavelength of 470 nm with respect to changes in the excited wavelength, while the fluorescence spectrum indicates such fluorescence spectrum at the excited wavelength of 420 nm. On comparing FIGS. 8 and 9, it will be seen that a well-matched behaviour is exhibited at the fluorescence excitation spectrum in a wavelength range of from 380 nm to 440 nm, and at the fluorescence spectrum in a wavelength range of from 450 nm to 490 nm, hence the fluorescence properties of the digested sludge in the above-mentioned wavelength ranges is derived from the Methanogens.

Figure 10:
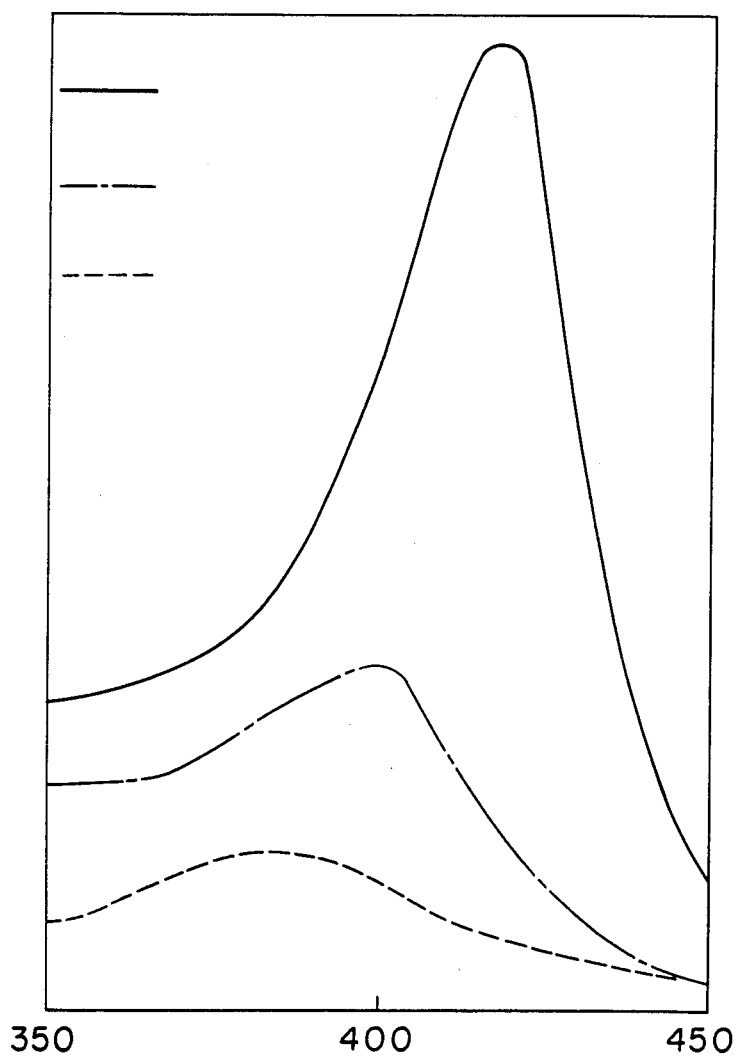
FIG. 10 is a characteristic curve showing variations in the fluorescence properties of Methanogens and *Escherichia coli* due to pH value.

FIG. 10 shows the fluorescence excitation spectrum of Methanogens and *Escherichia coli* in the nutrient medium at the respective pH values. The fluorescence excitation spectrum indicates an intensity of fluorescence having a wavelength of 470 nm with respect to changes in the excited wavelength. From the graphical representation, it will be seen that substantially no changes have taken place in the fluorescence excitation spectrum with *Escherichia coli* in the pH values ranging from 7 to 11, while the fluorescence excitation peak wavelength and its intensity vary depending on the pH value with Methanogens, the peak wavelength shifting by about 20 nm to the long wavelength side at the pH value of 11 as contrasted to the pH value 7, and the peak intensity also increasing as high as about three times. In this way, by addition of basic solution or basic solid such as, for instance, sodium hydroxide, potassium hydroxide, ammonium hydroxide, and so on, it becomes possible to render the object for examination to be alkaline in a pH value range of from 7 to 14, to increase the signal intensity of a fluorescence signal derived from Methanogens, to shift the excited fluorescence wavelength range to the long wavelength side in a range of from zero to 30 nm, and to increase the S/N ratio with respect to a background fluorescence derived from those components other than Methanogens. In particular, as is apparent from FIGS. 8 to 10, when use is made of light having a wavelength range of from 410 nm to 430 nm as the excited light and light having a wavelength range from 460 nm to 480 nm as the fluorescence, the spectra of both fluorescence excitation and fluorescence can be measured in the vicinity of their peak points.

It is further possible to increase the S/N ratio of the fluorescence signal derived from Methanogens even by separating liquid component out of the solid and by substituting liquid components in the object for examination with a solution such as water, etc. which does not radiate fluorescence of a measuring wavelength range in the excited wavelength range by use of the centrifugal operation or the filtration operation, or others; or diluting the object for examination with a solution such as water, etc. which does not radiate fluorescence of a measuring wavelength range in the excited wavelength range. Further, in this case, if use is made of a basic solution such as, for example, sodium hydroxide, potassium hydroxide, and so forth as the solution which does not radiate fluorescence of a measuring wavelength range in the excited wavelength range, the effect of the above-mentioned alkalinity is also added.

From the above-mentioned result of studies and researches, it has been found out that the following methods may be adopted for measuring the cell counts or methane producing activity of Methanogens existing in a multitude of microorganism groups and foreign substances such as digested sludge, etc. in the methane fermentation tank, and so on.

(1) As the light for fluorescence excitation, use is made of light having a wavelength range of from 220 nm to 310 nm, and the cell counts and the methane producing activity of Methanogens is determined from the interrelationship between the intensity of the excitation spectrum and the cell counts or the methane producing activity. Since the excitation spectrum of Methanogens has its peak values in the above-mentioned wavelength range, in particular, in the wavelength ranges of from 220 nm to 255 nm and from 260 nm to 305 nm, the cell counts or the methane producing activity of Methanogens can be determined with high precision by measurement of the intensity of the excitation spectra in these two wavelength ranges.

(2) As the fluorescence, use is made of light having a wavelength range of from 330 nm to 370 nm, and the cell counts or the methane producing activity of Methanogens is determined on the basis of the interrelationship between the intensity of the fluorescence spectrum and the cell counts or the methane producing activity of Methanogens.

(3) As the light for fluorescence excitation, use is made of light having a wavelength range of from 380 nm to 440 nm, and the cell counts or the methane producing activity of Methanogens is determined on the basis of the interrelationship between intensity of the excitation spectrum and the cell counts or the methane producing activity of Methanogens.

(4) As the fluorescence, use is made of light having a wavelength range of from 450 nm to 490 nm, and the cell counts or the methane producing activity of Methanogens is determined on the basis of the interrelationship between intensity of the fluorescence spectrum and the cell counts or the methane producing activity of Methanogens.

(5) As the methods for increasing the S/N ratio of the fluorescence derived from Methanogens with respect to the background fluorescence derived form the components other than Methanogens, the following three methods can be employed:
(a) the object for examination is rendered to be alkaline;
(b) the liquid component of the object for examination is substituted by other solution; and
(c) the object for examination is diluted.

Figure 6:
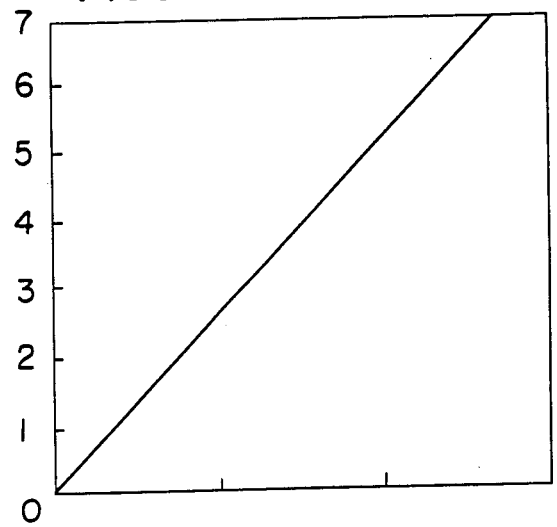
FIGS. 6 and 7 as well as FIGS. 11 and 12 are respectively graphical representations showing interrelationship between the cell counts of Methanogens and the intensity of excited spectrum of fluorescence as well as between the methane production quantity and the intensity of excited spectrum of fluorescence.
Figure 7:
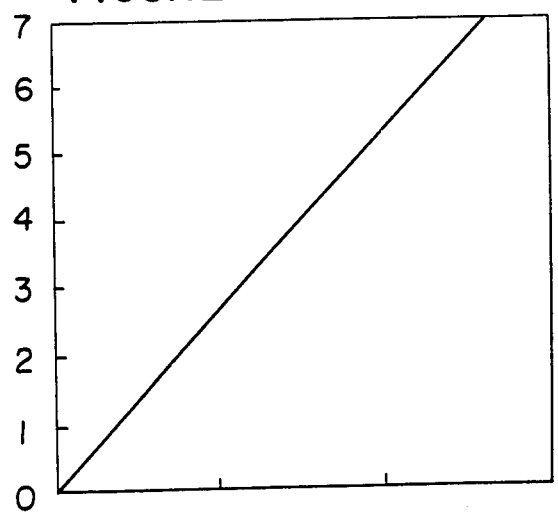
Figure 11:
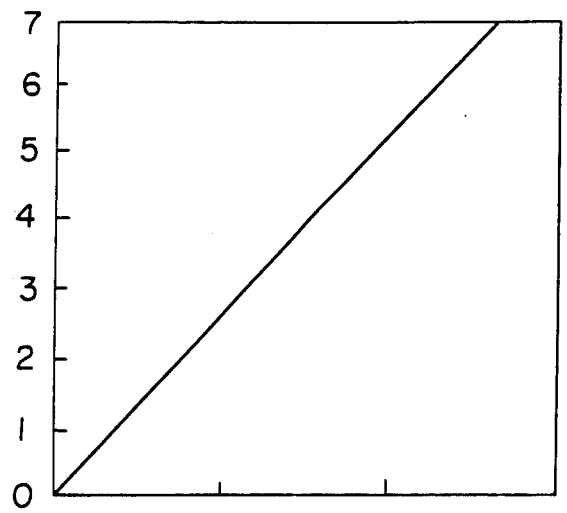
Figure 12:
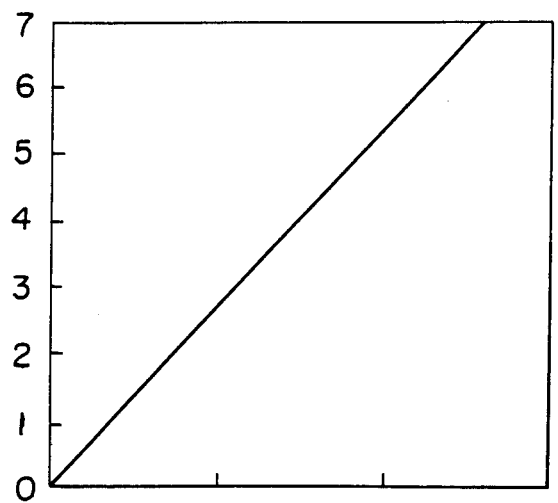

The interrelationship between the intensity of the fluorescence excitation spectrum or the fluorescence spectrum and the cell counts or the methane producing activity can be found from Methnomonas isolated from digested sludge, such as *Methnosarcina barkeri*, as a reference specimen. As examples of this, FIGS. 6 and 7 as well as FIGS. 11 and 12 respectively indicate the interrelationship between the cell counts and the intensity of the excitation spectrum as well as the interrelationship between the methane producing quantity and the intensity of the excitation spectrum. By the way, FIGS. 6 and 7 indicate the characteristics when use is made of light having a wavelength of 280 nm as the light used for the excitation, and light having a wavelength of 350 nm occurs as the fluorescence, while FIGS. 11 and 12 indicate the characteristics when use is made of light having a wavelength of 420 nm as the light used for the excitation, and the light having a wavelength of 470 nm occurs as the fluorescence.

According to such method of measurement, the cell counts or the methane producing activity of Methanogens can be measured real time during operation of the methane fermentation tank, hence remarkable effect can be expected in controlling operations of the methane fermentation tank.

Further, much convenience can be secured when the measuring system is constructed as shown in FIG. 2. That is to say, when a system controller is provided and wire-connected to the detector 19, the optical filters 12, 16, and so forth, there can be performed automatically by this system controller the operations such that an electric potential to be applied to the photoelectric multiplying tube 17 or intensity of the fluorescence excitation can be varied in accordance with intensity of light to be introduced into the photoelectric multiplying tube 17 to maintain the value of the photo-current flowing in the photoelectric multiplying tube 17 in a range suitable for the photoelectric multiplying tube 17, and, at the same time, the photo-current value with respect to each fluorescence excitation intensity or each applied voltage is converted to a photo-current value with respect to a certain definite fluorescence intensity or a certain definite applied voltage.

Furthermore, in the above-described embodiment, explanations have been given as to a method for measuring, wherein the optical fiber 9 is directly introduced into the interior of the methane fermentation tank 8, although it is also possible that the object for examination be sampled from the methane fermentation tank and measured outside the methane fermentation tank. For example, the object for examination is sampled from the methane fermentation tank through a sampling line, and the sampled object is supplied to a sample adjuster by means of a sampler part having a pumping function. In the sample adjuster, the object is adjusted to a condition suitable for measurement, and then, supplied to the optical measurement part. The measurement is conducted in the same manner as in the embodiment of FIG. 2. Thus, such a system can be constructed without using the optical fibers as shown in FIG. 2. When the object for examination is subjected to the alkaline treatment, or to dilution, or the substitution of the liquid component of the object for examination for other solution, such sampling of the object for examination would facilitate its treatment.

In addition, when Methanogens are immobilized to a immobilizing carrier, it is also possible to measure the object for examination at a position of immobilized Methanogens by use of the optical fiber 9.

In the foregoing explanations of the invention, the measurement of the cell counts or the methane producing activity of Methanogens existing in a multitude of microorganism groups and foreign substances such as digested sludge, etc. within the methane fermentation tank has been described in the main, although the invention is not limited to such object for examination.

As described in the foregoing, the present invention makes it possible to measure the cell counts or the methane producing activity of Methanogens based on measurement of intensity of fluorescence in a particular wavelength range to be radiated from the above-mentioned object for examination by irradiation of excitation light of a particular wavelength range onto the object for examination containing therein Methanogens. In particular, even from the mixed system of microorganism containing therein foreign substances, measurement of the cell counts or the methane producing activity of Methanogens can be done effectively.

INDUSTRIAL UTILITY

The present invention is applicable to measurement of the cell counts or the methane producing activity of Methanogens existing in a multitude of microorganism groups and foreign substances such as digested sludge, etc. in the methane fermentation tank, etc. for the waste water treating system.

We claim:

1. An apparatus for measuring cell counts or methane producing activity of Methanogens contained within a vessel comprising:
   a light source means for generating light of a particular wavelength;
   a first optical fiber means operatively associated with said light source means for transmitting the light from said light source means into said vessel causing the Methanogens to fluoresce;
   a second optical fiber means having one end disposed inside said pressure vessel for collecting the light flowered by the Methanogens contained within said vessel;
   a photo-electric multiplying means operatively associated with the end of said second optical fiber opposite that end of said second optical fiber means which is disposed within said vessel; and
   a detector coupled to said photo-electric multiplying means for measuring the photo current produced by said photo-electric multiplying means.

2. An apparatus as in claim 1 wherein a filter is disposed between said light source means and said first optical fiber means for passing light having a wavelength of 220 nm to 310 nm.

3. An apparatus as in claim 1 wherein a filter is disposed between said light source means and said first optical fiber means for passing light having a wavelength of 220 nm to 255 nm.

4. An apparatus as in claim 1 wherein a filter is disposed between said light source means and said first optical fiber means for passing light having a wavelength of 260 nm to 305 nm.

5. An apparatus as in claim 1 wherein a filter is disposed between said light source means and said first optical fiber means for passing light having a wavelength of 330 nm to 370 nm.

6. An apparatus as in claim 1 wherein a filter is disposed between said light source means and said first optical fiber means for passing light having a wavelength of 380 nm to 440 nm.

7. An apparatus as in claim 1 wherein a filter is disposed between said second optical fiber means and said photo-elective multiplying means for passing light have a wavelength of 450 nm to 490 nm.

8. An apparatus as in claim 1, further comprising:
means for rendering alkaline the material within a sample adjuster.

9. An apparatus as in claim 1 further comprising:
means for substituting the liquid component of the material contained within a sample adjuster with a solution that does not fluoresce in the measured wavelength range.

10. An apparatus as in claim 1 for measuring cell counts or methane producing activity of Methanogens contained within a vessel further comprising:
a sampling line means for sampling the material within said vessel;
a sample adjuster means for adjusting said material to a condition suitable for measurement;
an optical measurement part means for measuring the light fluoresced by the Methanogens in the material; and
a sampler part having a pumping function means for sampling the material from said vessel and supplying the material to said sample adjuster and optical measurement part.

11. A method for measuring cell counts or methane producing activity of Methanogens, characterized in that excited light having a wavelength range of from 380 nm to 440 nm is irradiated onto a material containing therein Methanogens, and then intensity of the light fluoresced by the Methanogens in the material, is measured, thereby obtaining the cell counts or the methane producing activity of said Methanogens, wherein the material is rendered alkaline and/or the liquid component of said material is substituted by a solution which does not fluoresce in the measured wavelength range in the excited wavelength range.

12. A method for measuring cell counts or methane producing activity of Methanogens, characterized in that excited light having a wavelength range of from 380 nm to 440 nm is irradiated onto a material containing therein Methanogens, and then intensity of the light fluoresced by the Methanogens in the material, is measured, thereby obtaining the cell counts or the methane producing activity of said Methanogens, wherein the material is rendered alkaline and/or the material is diluted with a solution which does not fluoresce in the measured wavelength range in the excited wavelength range.

* * * * *